United States Patent
Kosaka et al.

(10) Patent No.: US 6,479,549 B2
(45) Date of Patent: *Nov. 12, 2002

(54) CARNOSIC ACID DERIVATIVES FOR PROMOTING SYNTHESIS OF NERVE GROWTH FACTOR

(75) Inventors: Kunio Kosaka, Kobe (JP); Toshitsugu Miyazaki, Kobe (JP); Toshio Yokoi, Akashi (JP)

(73) Assignee: Nagase & Company, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/794,234

(22) Filed: Feb. 28, 2001

(65) Prior Publication Data

US 2001/0034370 A1 Oct. 25, 2001

(30) Foreign Application Priority Data

Feb. 28, 2000 (JP) ........................................ 2000-104172

(51) Int. Cl.$^7$ .................. A61K 31/19; A61K 31/21; C07C 67/02; C07C 63/44
(52) U.S. Cl. .................. 514/569; 514/510; 560/56; 560/249; 560/256; 562/466; 562/467
(58) Field of Search .................. 560/5, 56, 249, 560/256; 562/466, 403, 975, 467; 514/560, 732, 510, 569

(56) References Cited

U.S. PATENT DOCUMENTS

| | | | |
|---|---|---|---|
| 4,450,097 A | | 5/1984 | Nakatani et al. ............ 252/404 |
| 4,985,458 A | * | 1/1991 | Nakayama et al. |
| 5,023,017 A | | 6/1991 | Todd, Jr. .................... 252/407 |
| 5,256,700 A | * | 10/1993 | Aeschbach et al. |

FOREIGN PATENT DOCUMENTS

| | | |
|---|---|---|
| JP | 7-25777 | 1/1995 |
| JP | 7-173059 | 7/1995 |

OTHER PUBLICATIONS

Gonzolez et al. Oxidation Reactions of Carnosic Acid Derivatives, 1988, Journal of Chemical Research, Synopses, 4, pp. 114–15. Abstract only.*
Bruno et al., Abietane Diterpenoids from Lepechinia Meyeni and Lepechinia Hastata, 1991, Phytochemistry, 30(7), pp. 2339–2343.*
Duke, 1997, The Green Pharmacy, St. Martins Press, New York, N.Y., pp. 46–48.*
Emmett et al., Evaluation of Human Astrocytoma and Glioblastoma Cell Lines for Nerve Growth Factor Release, Neurochem, Int., vol. 30, No. 4/5, pp. 465–474 (1997).
Boutros et al., Interferon–β is a Potent Promoter of Nerve Growth Factor Production by Astrocytes, J. Neurochemistry, vol. 69, No. 3, pp. 939–946 (1997).
Offord et al., Rosemary Components Inhibit Benzol[β]Pyrene–Induced Genotoxicity in Human Bronchial Cells, Carcinogenesis, vol. 16, No. 9, pp. 2057–2062 (1995).
Paris et al., Inhibitory Effect of Carnosolic Acid on HIV–1 Protease in Cell–Free Assays, J. Natural Products, vol. 56, No. 8, pp. 1426–1430 (1993).
Huang et al., Inhibition of Skin Tumorigenesis by Rosemary and ITS Constituents Carnosol and Ursolic Acid, Cancer Res., Feb., No. 54, pp. 701–708 (1994).
Smith et al., Protection by Albumin Against the Pro–Oxidant Actions of Phenolic Dietary Components, Food Chem. Toxic., vol. 30, No. 6, pp. 483–489 (1992).
Aruoma et al., An Evaluation of the Antioxidant and Antiviral Action of Extracts of Rosemary and Provençal Herbs, Food Chem. Toxic, No. 34, pp. 449–456 (1996).
Pearson et al., Inhibition of Endothelial Cell–Mediated Oxidation of Low–Density Lipoprotein by Rosemary and Plant Phenolics, J. Agric. Food Chem., No. 45, pp. 578–582 (1997).
Chan et al., Effects of Three Dietary Phytochemicals from Tea, Rosemary and Turmeric on Inflammation–Induced Nitrite Production, Cancer Lett., vol. 96, No. 1, pp. 23–29 (1995).
Laughton et al., Inhibition of Mammalian 5–Lipoxygenase and Cyclo–Oxygenase by Flavonoids and Phenolic Dietary Additives, Biochem. Pharmacol., vol. 42, No. 9, pp. 1673–1681 (1991).
Kawagishi et al., Hericenones C, D and E, Stimulators of Nerve Growth Factor (NGF)–Synthesis, from the Mushroom *Hericium Erinaceum*, Tetrahedron Lett, vol. 32, pp. 4561–4564 (1991).
Kawagishi et al., Chromans, Hericenones F, G and H from the Mushroom *Hericium Erinaceum*, Phytochemistry, vol. 32, pp. 175–178, (1993).
Shinoda et al., Stimulation of Nerve Growth Factor Synthesis/Secretion by Propentofylline in Cultured Mouse Astroglial Cells, Biochem. Pharm., vol. 39, pp. 1813–1816 (1990).
Yamaguchi et al., Stimulation of Nerve Growth Factor Production by Pyrroloquinoline Quinone and its Derivaties In Vitro and In Vivo, Biosci. Biotech. Biochem., vol. 57, pp. 1231–1233 (1993).

* cited by examiner

*Primary Examiner*—Sreeni Padmanabhan
*Assistant Examiner*—Paul A. Zucker
(74) *Attorney, Agent, or Firm*—Jacobson Holman, PLLC

(57) ABSTRACT

A novel carnosic acid derivative for promoting the synthesis of nerve growth factor (NGF), a composition comprising the carnosic acid derivative as an effective ingredient, as well as, a method of promoting the synthesis of NGF comprising administering an effective amount of the carnosic acid derivative as an effective ingredient to a subject requiring such promotion. The carnosic acid derivative, composition and method according to the present invention can safely and efficiently promote the production of NGF in the living body, without being accompanied by a side effect such as a loss of a quantitative balance of hormones in the living body.

4 Claims, No Drawings

CARNOSIC ACID DERIVATIVES FOR PROMOTING SYNTHESIS OF NERVE GROWTH FACTOR

Priority rights based upon Japanese Application No. 104172/2000, filed Feb. 28, 2000, are claimed under 35 U.S.C. §119.

FIELD OF THE INVENTION

The present invention relates to a novel carnosic acid derivatives for promoting the synthesis of nerve growth factor, more particularly, a carnosic acid derivative capable of efficiently promoting the synthesis of nerve growth factor in the treatment of nerve-denaturing diseases such as Alzheimer-type dementia and brain ischemia pathologies. The present invention also relates to a composition comprising the carnosic acid derivative as well as a method of promoting the synthesis of nerve growth factor.

DESCRIPTION OF THE PRIOR ART

Senile dementia has a tendency to increase with the shift to an aging society. This tendency has become an extremely large social problem. A number of diseases are known which are responsible for senile dementia. They are roughly divided into dementia attributable to an organic disorder of the brain, dementia incidental to a disease of other organs than the brain, and dementia attributable to a physical disease due to stress. In particular, the dementia attributable to an organic disorder of the brain, which constitutes a greater part of the causes of dementia, is divided into cerebrovascular dementia and Alzheimer-type dementia due to the differences of the causes.

Currently, it has been known that a drug such as a cerebrovascular dilator exhibits a certain effect on the cerebrovascular dementia. However, the causes of development of Alzheimer-type dementia are not known yet, and a pharmacotherapy and other treating methods suitable for preventing the development and progression of the dementia are not known yet. Accordingly, it is greatly desired to develop a drug useful for the treatment of dementia due to an organic disorder of the brain, in particular, Alzheimer-type dementia.

Recently, it has been found that a neurotrophic factor such as nerve growth factor (NGF) secreted from nerve cells has an excellent effect on nerve-denaturing diseases, and special attention has been paid to the factor. NGF is a factor necessary and important to the growth and functional maintenance of the nervous tissue. NGF is essential formaturation, differentiation and survival of sensory and sympathetic nerves in the peripheral nervous system as well as for those of large cell cholinergic neurons in the central nervous system. Also, NGF exhibits an effect of preventing denaturing of nerve cells when undergoing a brain lesion. Accordingly, it is believed that an elevation of the NGF level in the living body is effective for treating a disorder of central functions (including Alzheimer-type dementia and cerebrovascular dementia), a lesion of peripheral nerves, a diabetic neuropathy and a disorder of peripheral functions (including amyotrophic lateral sclerosis).

However, NGF is a protein having a high molecular weight of about 13,000 in its monomer form and about 26,000 in its dimer form, and can not pass through the blood-brain barrier. Accordingly, it is necessary to administer NGF intraventricularly, for example, when the treatment of a disorder of central functions is aimed. In addition, it is difficult to prepare NGF in a large amount. Thus, it is very problematic to use NGF per se. Consequently, it is very difficult to use NGF per se clinically.

A method of administering a substance for promoting the synthesis of NGF in the living body, instead of NGF, is also known in the art. For example, Y. Furukawa et al. (FEBS Lett., Vol.208 (1986), p.258 et seq.) discloses that catecholamines (epinephrine, norepinephrine and dopamine) are used as the substance for promoting the synthesis of NGF.

However, they are hormone substances, and therefore, the administration of them causes a problem of losing a quantitative balance of hormones in the living body.

The present invention is addressed to the solution of the above problems.

Thus, the object of the present invention is to provide a substance capable of promoting an effective synthesis of NGF in the living body.

Another object of the present invention is to provide a composition for promoting the synthesis of NGF in the living body.

Other object of the present invention is to provide a method of promoting the synthesis of NGF in the living body.

SUMMARY OF THE INVENTION

The present inventors have intensively searched for a substance having a potent effect of promoting the synthesis of NGF. As a result, they found that carnosic acid derivatives of the following formula (I) have such an effect:

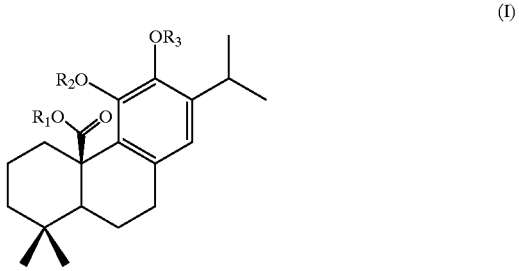

(I)

wherein $R_1$ is a hydrogen atom or a $C_1$–$C_5$ alkyl group, and $R_2$ and $R_3$ independently of one another are a hydrogen atom, a $C_1$–$C_5$ alkyl group or a $C_1$–$C_5$ acyl group, provided that at least one of $R_1$, $R_2$ and $R_3$ is not a hydrogen atom.

Thus, the present invention provides a carnosic acid derivative of the above formula (I).

Also, the present invention provides a composition for promoting the synthesis of nerve growth factor comprising a carnosic acid derivative of the above formula (I) as an effective ingredient.

Furthermore, the present invention provides a method of promoting the synthesis of nerve growth factor comprising administering an effective amount of a carnosic acid derivative of the above formula (I) as an effective ingredient to a subject requiring such promotion.

A preferred carnosic acid derivative is a compound of the above formula (I) wherein $R_1$ is a hydrogen atom, and both $R_2$ and $R_3$ are acetyl groups.

Another preferred carnosic acid derivative is a compound of the above formula (I) wherein $R_1$ is a methyl group, and both $R_2$ and $R_3$ are hydrogen atoms.

DETAILED DESCRIPTION OF THE INVENTION

The present invention is described in more detail in the following.

The present carnosic acid derivatives of the above formula (I) may be prepared by chemically modifying carnosic acid of the following formula (II):

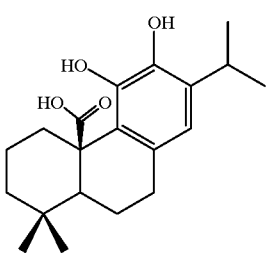
(II)

Although carnosic acid of the above formula (II) may be prepared by chemical synthesis, it is advantageous to obtain it by extraction from a plant containing carnosic acid, for example, from rosemary (Rosmarinus officinalis L.) or sage (Salvia officinalis L.).

For example, rosemary or sage may be extracted in the following manner. Firstly, the whole plant, leaves and/or petals of rosemary or sage are soaked in ethanol or an aqueous ethanol solution having an ethanol concentration of 80% (v/v) to 100% (v/v) to obtain an extract. Typical extraction conditions include a temperature of about 0° C. to about 50° C. and an extraction time of about one hour to about 48 hrs.

Then, water is added to the extract so as to give an ethanol concentration of not greater than 40% (v/v). By doing so, it is possible to deposit a precipitate containing carnosic acid from the extract. Alternatively, the above extract may be concentrated to one-half to one-twentieth of its original volume, and then, water may be added to the concentrate to deposit a precipitate containing carnosic acid. Typical deposition conditions include a temperature of about 0° C. to about 25° C. and a deposition time of about one hour to about 48 hrs.

By repeating several times the step of adding ethanol or water to the extract so as to give a particular ethanol concentration, the step of dissolving or depositing a precipitate, and the step of filtration, it is possible to obtain a precipitate containing carnosic acid of the formula (II) in a large amount.

Subsequently, carnosic acid of the formula (II) can be obtained by removing impurities from the precipitate through various column chromatographic means. Those skilled in the art can easily identify by well known means such as $^1$H-NMR or $^{13}$C-NMR that the substance thus obtained is carnosic acid of the formula (II).

The present carnosic acid derivatives of the above formula (I) may be prepared from the carnosic acid in the following manner.

Thus, the derivatives of the above formula (I), wherein $R_1$ is a $C_1$–$C_5$ alkyl group, may be prepared by a known esterification method in the art. For example, they may be prepared by reacting carnosic acid with an alcohol such as methanol, ethanol, propanol, butanol or pentanol in the presence of an acid such as hydrogen chloride, sulfuric acid or p-toluenesulfonic acid. Alternatively, the methyl-esterified derivative may be prepared by using a diazomethane ether solution.

The derivatives of the above formula (I), wherein $R_2$ and $R_3$ are $C_1$–$C_5$ acyl groups, may be prepared by reacting carnosic acid with an appropriate acid anhydride or acid halide in the presence of a base such as triethylamine or pyridine.

The derivatives of the above formula (I), wherein $R_1$, $R_2$ and $R_3$ are $C_1$–$C_5$ alkyl groups, may be prepared by reacting carnosic acid with an appropriate alkyl halide in the presence of a base such as sodium hydride or sodium amide.

The above reaction may be carried out in an appropriate solvent. Examples of the solvent include chloroform, diisopropyl ether, acetone, methyl ethyl ketone, dioxane, dichloromethane, diethyl ether, tetrahydrofuran, toluene, benzene, xylene, n-hexane and heptane.

If it is necessary to prepare the derivatives of the above formula (I) wherein $R_1$ is a hydrogen atom, and $R_2$ and $R_3$ are $C_1$–$C_5$ alkyl groups, the derivatives of the above formula (I), wherein $R_1$, $R_2$ and $R_3$ are $C_1$–$C_5$ alkyl groups, may be hydrolyzed by using an aqueous alkali solution such as an aqueous sodium hydroxide or potassium hydroxide solution.

The present composition for promoting the synthesis of nerve growth factor comprises a carnosic acid derivative of the above formula (I) as an effective ingredient. The content of the above derivative contained in the composition is preferably about 0.00001% by weight to less than 100% by weight, more preferably about 0.001% by weight to less than 100% by weight, per 100% by weight of the composition. If the content of the derivative is less than 0.00001% by weight, the composition can not promote the production of NGF sufficiently.

The carnosic acid derivatives of the above formula (I) may be made up into suitable forms such as food or drug compositions. Also, the compositions according to the present invention may be used for both of oral administration and parenteral administration.

In case of making up into food compositions, the above derivatives are mixed with suitable materials which may be commonly used as food materials. Examples of the food materials are rice, wheat, corn, potato, sweet potato, soybean, sea tangle, wakame (Undaria pinnatifida), agar weed; starch syrup; sugars such as lactose, glucose, fructose, sucrose, mannitol; and combinations of these materials. In addition, flavoring agents, coloring agents, sweetening agents, edible oils, vitamins and the like may be added to the food compositions. These materials and additives may be used alone or in combination with one another. Also, the food compositions may be made up into a desired shape, if necessary, by adding water.

In case of making up into drug compositions, the above derivatives are mixed with suitable additives. Examples of the additives are surfactants, excipients, coloring agents, preservatives, coating aids and combinations of these additives. These additives may be those commonly used in the production of drug compositions and are not limited to particular ones. More specific examples of the additives are lactose, dextrin, sucrose, mannitol, corn starch, sorbitol, crystalline cellulose, polyvinylpyrrolidone and combinations of these additives. Also, flavoring agents, sweetening agents and the like may be added to the drug compositions. In addition, other drugs may be added to the drug compositions, if necessary.

There is no limitation in dosage forms of the drug compositions and they may be produced in suitable dosage forms according to a conventional process. For oral administration, in particular, the compositions may be prepared in the forms of capsules, tablets, powder, slow-releasing agents and the like. For parenteral administration, the compositions may be prepared in the forms of injections, infusions and the like.

There is no limitation in the content of the above suitable materials and additives, and they may be used depending on the content of the carnosic acid derivatives of the above formula (I).

EXAMPLES

The present invention is illustrated in more detail by the following examples, but it is not limited thereto.
PREPARATION 1
Preparation of Carnosic Acid
Rosemary (whole plant, 5 kg) was soaked in ethanol (20 L), and extracted at 40° C. for 72 hrs. The resultant solution was concentrated to a volume of 1 L. After the concentration, the concentrate was filtered to remove insoluble materials. Purified water (2 L) was added to the filtrate and the precipitate (105 g) deposited at this time was filtered. The precipitate was dissolved in ethyl acetate, and separated and purified through a silica gel column chromatography (developing solvent; ethyl acetate:hexane=1:4 (v/v)). The residue obtained by removing the solvent was recrystallized in hexane to obtain 1.5 g of pale yellow crystals (Compound A).

$^{13}$C-NMR and $^1$H-NMR spectra (CDCl$_3$) of Compound A are shown in the following Table 1. From the NMR spectra, Compound A was identified to be carnosic acid of the above formula (II).

TABLE 1

NMR spectra of Compound A

| $^{13}$C δ(ppm), CDCl$_3$, 125 MHz | $^1$H δ(ppm), CDCl$_3$, 500 MHz |
|---|---|
| 34.4(t); 20.3(t); | 1.24(1H, m) and 3.29(1H, m); |
| 41.8(t); 34.4(s); | 1.60(1H, m) and 1.75(1H, m); |
| 54.0(d); 18.9(t); | 1.32(1H, m) and 1.50(1H, dt); |
| 31.5(t); 129.0(s); | 1.57(1H, dd); |
| 122.1(s); 48.7(s); | 1.86(1H, m) and 2.36(1H, m); |
| 142.1(s); 141.4(s); | 2.85(2H, m); 6.64(1H, s); |
| 133.8(s); 119.4(d); | 3.17(1H, m); 1.21(3H, d); |
| 27.2(d); 22.1(q); | 1.20(3H, d); 0.89(3H, s); |
| 22.5(q); 32.6(q); | 1.00(3H, s); 6.56(2H, s); |
| 21.7(q); 183.1(s) | 7.36(1H, s) |

EXAMPLE 1

Synthesis of Carnosic Acid Diacetate

Carnosic acid (712 mg) obtained in Preparation 1 was dissolved in pyridine (3 ml). Acetic anhydride (3 ml) was added to the solution and the mixture was allowed to stand overnight at room temperature. After the completion of the reaction, water (20 ml) was added to the mixture to decompose an excess of acetic anhydride. The mixture was extracted three times with chloroform (50 ml). The extract was washed with dilute hydrochloric acid and then dried over magnesium sulfate. Chloroform was distilled off to obtain 950 mg of an oily residue. The oily residue was separated and purified through a preparative thin-layer chromatography (Merck Co. Silica gel PF254; developing solvent: ethyl acetate:hexane=1:2 (v/v)) to obtain 743 mg of a crystalline residue. The residue was recrystallized in ethyl acetate-hexane to obtain 651 mg of colorless rod crystals (Compound B; m.p. 215–217° C.).

$^{13}$C-NMR and $^1$H-NMR spectra (CDCl$_3$) of Compound B are shown in the following Table 2. From the NMR spectra, Compound B was identified to be carnosic acid diacetate of the following formula (III).

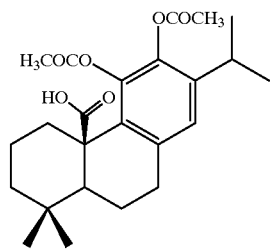

(III)

TABLE 2

NMR spectra of Compound B

| $^{13}$C δ(ppm), CDCl$_3$, 125 MHz | $^1$H δ(ppm), CDCl$_3$, 500 MHz |
|---|---|
| 18.1(t), 19.9(t), | 6.94(1H, s), 3.20(1H, brd), |
| 20.1(q), 20.4(q), | 2.81–2.75(3H, m), |
| 20.5(q), 22.7(q), | 2.34(1H, m), 2.24(3H, s), |
| 23.0(q), 27.4(d), | 2.22(3H, s), 2.11(1H, m), |
| 31.9(t), 32.5(q), | 1.82(1H, dd), |
| 34.0(s), 34.5(t), | 1.54–1.45(3H, m), |
| 41.1(t), 47.7(s), | 1.30–1.20(2H, m), |
| 53.8(d), 125.1(d), | 1.15(3H, d), 1.13(3H, s), |
| 132.3(s), 136.8(s), | 0.95(3H, s), 0.85(3H, s) |
| 138.6(s), 139.8(s), | |
| 141.3(s), 168.3(s), | |
| 168.7(s), 180.4(s) | |

EXAMPLE 2

Synthesis of Carnosic Acid Diacetate Methyl Ester

Carnosic acid diacetate (375 mg) obtained in Example 1 was dissolved in chloroform (1.5 ml) and a diazomethane-ether solution (2.5 ml) previously prepared was added to the solution. After three minutes, acetic acid (0.5 ml) was added to the solution to decompose an excess of diazomethane. Water (15 ml) was added to the solution and the mixture was extracted three times with chloroform (25 ml). The chloroform layers were combined, washed with water and then dried over magnesium sulfate. The solvent was distilled off under reduced pressure to obtain 395 mg of an oily residue. The residue was separated and purified through a preparative thin-layer chromatography as described above, to obtain 305 mg of an oily substance (Compound C).

$^{13}$C-NMR and $^1$H-NMR spectra (CDCl$_3$) of Compound C are shown in the following Table 3. From the NMR spectra, Compound C was identified to be carnosic acid diacetate methyl ester of the following formula (IV).

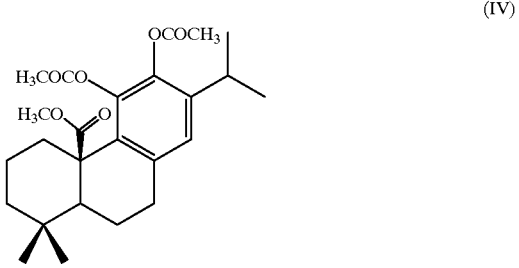

(IV)

TABLE 3

NMR spectra of Compound C

| $^{13}$C δ(ppm), CDCl$_3$, 125 MHz | $^1$H δ(ppm), CDCl$_3$, 500 MHz |
|---|---|
| 175.2(s), 168.6(s), | 6.95(1H, s), 3.51(3H, s), |
| 168.2(s), 141.4(s), | 3.28(1H, brd), 2.91(2H, m), |
| 139.7(s), 138.8(s), | 2.88(1H, septet), |
| 136.7(s), 131.8(s), | 2.31(1H, m), 2.25(3H, s), |
| 125.1(d), 53.6(d), | 2.24(3H, s), 2.10(1H, m), |
| 51.7(q), 47.8(s), | 1.85(1H, brd), 1.54(1H, m), |
| 41.1(t), 34.7(t), | 1.53(1H, dd), 1.47(1H, dt), |
| 34.0(s), 32.5(q), | 1.30–1.24(2H, m), |
| 31.9(t), 27.4(d), | 1.21(3H, d), 1.14(3H, d), |
| 23.0(q), 22.7(q), | 0.96(3H, s), 0.74(3H, s) |

TABLE 3-continued

NMR spectra of Compound C

| $^{13}C$ δ(ppm), CDCl$_3$, 125 MHz | $^1H$ δ(ppm), CDCl$_3$, 500 MHz |
|---|---|
| 20.7(q), 20.4(q), 19.9(t), 19.8(q), 18.4(t) | |

EXAMPLE 3

Synthesis of Carnosic Acid Methyl Ester

Carnosic acid (574 mg) obtained in Preparation 1 was dissolved in chloroform (5 ml) and the diazomethane-ether solution (3 ml) described above was added to the solution. After one minute, acetic acid (1 ml) was added to the solution. Water (20 ml) was added to the solution and the mixture was extracted three times with chloroform (30 ml). The chloroform layers were combined, washed with water and then dried over magnesium sulfate. The chloroform solution was concentrated under reduced pressure to obtain 671 mg of an oily residue. The residue was separated and purified through a preparative thin-layer chromatography to obtain 590 mg of a substance (Compound D).

$^{13}$C-NMR and H-NMR spectra (CDCl$_3$) of Compound D are shown in the following Table 4. From the NMR spectra, Compound D was identified to be carnosic acid methyl ester of the following formula (V).

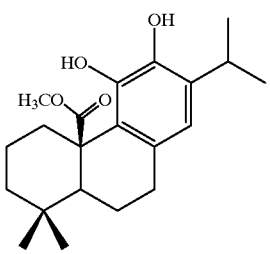

(V)

TABLE 4

NMR spectra of Compound D

| $^{13}C$ δ(ppm), CDCl$_3$, 125 MHz | $^1H$ δ(ppm), CDCl$_3$, 500 MHz |
|---|---|
| 178.8(s), 142.1(s), | 7.46(1H, brd), 6.54(1H, s), |
| 141.7(s), 133.3(s), | 5.81(1H, brd), 3.66(3H, s), |
| 128.5(s), 122.1(s), | 3.31(1H, dt), |
| 119.2(d), 54.0(d), | 3.20(1H, septet), |
| 52.1(q), 49.1(s), | 2.82–2.70(2H, m), |
| 42.0(t), 35.0(t), | 2.29(1H, m), 1.86(1H, m), |
| 34.3(s), 32.6(t), | 1.68(1H, m), 1.61(1H, m), |
| 31.6(t), 27.2(d), | 1.56(1H, dd), 1.46(1H, dt), |
| 22.5(q), 22.1(q), | 1.31(1H, m), 1.24(1H, m), |
| 21.8(q), 20.4(t), | 1.22(3H, d), 1.20(3H, d), |
| 19.2(t) | 1.00(3H, s), 0.80(3H, s) |

EXAMPLE 4

Human glioblastoma cells (T98G cell line) were seeded in a MEM medium containing fetal bovine serum (10%; Gibco), sodium pyruvate (x 1; Gibco) and nonessential amino acids (x 1; Gibco) in wells of a flat-bottom 96-well plate (Corning), in a cell density of 2×10$^4$/well, and cultivated in a CO$_2$ incubator (37° C., 5% CO$_2$) for 3 days. The medium was then replaced by an Opti-MEM medium (containing 5 mg/ml of bovine serum albumin). The cultivation was continued for further 6 days with replacing the medium at intervals of 3 days.

After removing the medium, an Opti-MEM medium (containing 5 mg/ml of bovine serum albumin) containing 100 uM (micromole) of carnosic acid diacetate obtained in Example 1 was added to each well in an amount of 50 ul (microliter)/well, and the cultivation was continued for further 4 days. After the cultivation, the supernatant was taken as a sample solution.

On the other hand, 1 ug/ml of an anti-NGF antibody (Promega) solution (50 ul) was added to each well of a 96-well microplate (Nunc), and the plate was allowed to stand overnight at 4° C. After washing the plate with PBS(-) (Nissui Pharmaceuticals), 1% of a bovine serum albumin (Sigma) solution (100 ul) was added to each well of the plate and the plate was allowed to stand at room temperature for 4 hrs to block the plate. Subsequently, the plate was washed with PBS(-) and the above sample solution (50 ul) was added to each well of the plate. After the reaction at room temperature for one hour, the plate was washed with PBS(-).

Subsequently, 0.4 unit/ml of a beta-galactosidase-labeled anti-NGF antibody (Boehringer Mannheim) solution (50 ul) was added to each well of the plate, and allowed to react at room temperature for one hour. After washing the plate with PBS (-), 0.5 mg/ml of a 4-methylumbelliferyl-beta-D-galactoside solution (200 ul) was added to each well of the plate, and allowed to react overnight at room temperature. The fluorescence intensity of 4-methylumbelliferone produced was measured on a fluorescence plate reader, and the content of NGF contained in the sample solution was determined using a standard curve obtained from a standard solution (human beta-NGF; PEPRO TECH EC). The results are shown in Table 5 below.

EXAMPLE 5

The content of NGF contained in the sample solution was determined as described in Example 4, except that an Opti-MEM medium (containing 5 mg/ml of bovine serum albumin) containing 100 uM of carnosic acid diacetate methyl ester obtained in Example 2 was used in an amount of 50 ul/well, instead of carnosic acid diacetate. The results are shown in Table 5 below.

EXAMPLE 6

The content of NGF contained in the sample solution was determined as described in Example 4, except that an Opti-MEM medium (containing 5 mg/ml of bovine serum albumin) containing 100 uM of carnosic acid methyl ester obtained in Example 3 was used inan amount of 50 ul/well, instead of carnosic acid diacetate. The results are shown in Table 5 below.

COMPARATIVE EXAMPLE 1

The content of NGF contained in the sample solution was determined as described in Example 4, except that an Opti-MEM medium (containing 5 mg/ml of bovine serum albumin) not containing carnosic acid diacetate was used in an amount of 50 ul/well, instead of the Opti-MEM medium containing carnosic acid diacetate. The results are shown in Table 5 below.

TABLE 5

| | Effective ingredient | Concentration (uM)*1 | NGF Content in sample solution (pg/ml)*2 | Relative NGF content*3 |
|---|---|---|---|---|
| Example 4 | Carnosic acid diacetate | 100 | 203.5 ± 11.6 | 32.3 |
| Example 5 | Carnosic acid diacetate methyl ester | 100 | 50.6 ± 4.3 | 8.0 |
| Example 6 | Carnosic acid methyl ester | 100 | 33.3 ± 2.8 | 5.3 |
| Comparative example 1 | none | 0 | 6.3 ± 1.2 | 1.0 |

*1: Concentration of effective ingredient in medium
*2: NGF Content shown by mean measurements ± standard deviation
*3: Ratio of NGF content in example solution to that in comparative example solution As shown in Table 5, it is evident that the content of NGF in the sample solution increases in the systems containing the carnosic acid derivative according to the present invention (Examples 4 to 6), as compared with the system not containing the derivative (Comparative Example 1).

EXAMPLE 7

To Wistar male rats (5 rats per group) of 180–200 g body weight fasted for 24 hours before the start of a test, carnosic acid diacetate obtained in Example 1 was orally administered in a dose level of 10 mg per kg body weight, after suspending it in water. After 30 minutes of the administration, 1 ml of ethanol (99.5%) was orally administered to each rat. After one hour of the ethanol administration, laparotomy was carried out and the lengths of all ulcers developed in the stomach were measured arld added up. The total lengths of ulcers are taken as ulcer indexes. The results are shown in Table 6 below.

EXAMPLE 8

The lengths of all ulcers developed in the stomach were measured and added up as described in Example 7, except that water containing carnosic acid methyl ester (10 mg per kg body weight) was used instead of water containing carnosic acid diacetate. The total lengths of ulcers are taken as ulcer indexes. The results are shown in Table 6 below.

COMPARATIVE EXAMPLE 2

The lengths of all ulcers developed in the stomach were measured and added up as described in Example 7, except that water not containing carnosic acid diacetate was used instead of water containing carnosic acid diacetate. The total lengths of ulcers are taken as ulcer indexes. The results are shown in Table 6 below.

TABLE 6

| | Effective ingredient | dose level*1 | Ulcer index (mm)*2 | Relative ulcer index*3 |
|---|---|---|---|---|
| Example 7 | Carnosic acid diacetate | 10 | 52.7 ± 13.6 | 84.5 |
| Example 8 | Carnosic acid methyl ester | 10 | 33.6 ± 3.6 | 53.8 |
| Comparative example 2 | none | 0 | 62.4 ± 10 | 100 |

*1: mg/kg body weight
*2: Ulcer index shown by mean measurements ± standard deviation
*3: Ratio of ulcer index in example to that in comparative example 2

As shown in Table 6, it is evident that the ulcer index decreases in the systems containing the carnosic acid derivative according to the present invention (Examples 7 and 8), as compared with the system not containing the derivative (Comparative Example 2). Thus, it was found that the derivatives according to the present invention have an anti-ulcer action.

EXAMPLE 9

Capsules were prepared in the following manner. Carnosic acid diacetate obtained in Example 1 (10 mg), lactose (50 mg) and crystalline cellulose (50 mg) were mixed to obtain a mixture. An aqueous hydroxypropyl cellulose solution (5%) was sprayed on the mixture, and the mixture was subjected to fluidized bed granulation to obtain granules. A small amount of magnesium stearate (1%) was added to the granules and the resultant granules were filled into capsules.

According to the present invention, it is possible to efficiently promote the synthesis of NGF. The present carnosic acid derivatives can promote the production of NGF in the living body with a high safely, without being accompanied by a side effect such as a loss of a quantitative balance of hormones in the living body. It is expected by the increase of NGF in the living body that nerve-denaturing diseases such as Alzheimer-type dementia and brain ischemia pathologies are prevented and treated.

What is claimed is:

1. A method of promoting synthesis of nerve growth factor comprising administering an effective amount of a carnosic acid derivative of the general formula (I):

wherein $R_1$ is a hydrogen atom or a $C_1$–$C_5$ alkyl group, and $R_2$ and $R_3$, independently of one another, are a hydrogen atom, a $C_1$–$C_5$ alkyl group or a $C_1$–$C_5$ acyl group, provided that at least one of $R_1$, $R_2$ and $R_3$ is not a hydrogen atom, as an effective ingredient to a subject requiring such promotion.

2. The method according to claim 1 in which the carnosic acid derivative is that wherein $R_1$ is a hydrogen atom, and both $R_2$ and $R_3$ are acetyl groups.

3. The method according to claim 1 in which the carnosic acid derivative is that wherein $R_1$ is a methyl group, and both $R_2$ and $R_3$ are hydrogen atoms.

4. The method according to claim 1 in which the carnosic acid derivative is that wherein $R_1$ is a methyl group, and both $R_2$ and $R_3$ are acetyl groups.

* * * * *